(12) United States Patent
Sandor et al.

(10) Patent No.: US 10,379,249 B2
(45) Date of Patent: Aug. 13, 2019

(54) OIL VISCOSITY PREDICTION

(71) Applicant: Halliburton Energy Services, Inc., Houston, TX (US)

(72) Inventors: Magdalena Traico Sandor, Humble, TX (US); Songhua Chen, Katy, TX (US); Yuesheng Cheng, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 295 days.

(21) Appl. No.: 15/300,470

(22) PCT Filed: Dec. 1, 2015

(86) PCT No.: PCT/US2015/063097
§ 371 (c)(1),
(2) Date: Sep. 29, 2016

(87) PCT Pub. No.: WO2017/095390
PCT Pub. Date: Jun. 8, 2017

(65) Prior Publication Data
US 2018/0017699 A1 Jan. 18, 2018

(51) Int. Cl.
*G01V 3/00* (2006.01)
*G01V 3/32* (2006.01)
(Continued)

(52) U.S. Cl.
CPC ............... *G01V 3/32* (2013.01); *E21B 49/08* (2013.01); *G01N 11/00* (2013.01); *G01R 33/448* (2013.01);
(Continued)

(58) Field of Classification Search
CPC ...................................................... G01V 3/32
(Continued)

(56) References Cited

U.S. PATENT DOCUMENTS 6,111,408 A   8/2000  Blades et al.
6,420,869 B1  7/2002  Difoggio
(Continued)

FOREIGN PATENT DOCUMENTS

WO   WO2005091018 A1   9/2005

OTHER PUBLICATIONS

"International Application Serial No. PCT/US2015/063097, International Search Report dated Sep. 1, 2016", 3 pgs.
(Continued)

*Primary Examiner* — Louis M Arana
(74) *Attorney, Agent, or Firm* — Haynes and Boone, LLP

(57) ABSTRACT

Various embodiments include a method for determining a viscosity for heavy oil in a formation by obtaining viscosity data and nuclear magnetic resonance (NMR) relaxation time distribution data for a plurality of oil samples. A correlation is determined between a set of viscosity data for the plurality of oil samples and an NMR relaxation time geometric mean for the plurality of oil samples. An NMR relaxation time geometric mean intrinsic value is determined based on the correlation, apparent hydrogen index, and $T_E$. Electromagnetic energy may then be transmitted into a formation and NMR relaxation time distributions determined for oil in the formation based on secondary electromagnetic field responses associated with the electromagnetic energy. A viscosity of the oil in the formation may then be determined based a correlation between the set of viscosity data and the NMR relaxation time geometric mean intrinsic value of the distribution data.

20 Claims, 12 Drawing Sheets

(51) Int. Cl.
*G01V 3/14* (2006.01)
*E21B 49/08* (2006.01)
*G01N 11/00* (2006.01)
*G01R 33/44* (2006.01)
*E21B 47/18* (2012.01)
*G01N 24/08* (2006.01)
*G01N 33/28* (2006.01)

(52) U.S. Cl.
CPC ............... *G01V 3/14* (2013.01); *E21B 47/18* (2013.01); *E21B 2049/085* (2013.01); *G01N 24/081* (2013.01); *G01N 33/28* (2013.01)

(58) Field of Classification Search
USPC .................................................. 324/303, 306
See application file for complete search history.

(56) References Cited

U.S. PATENT DOCUMENTS

| | | | |
|---|---|---|---|
| 10,061,052 B2* | 8/2018 | Chen | G01V 3/32 |
| 2008/0204013 A1 | 8/2008 | Badry et al. | |
| 2013/0265055 A1 | 10/2013 | Mitchell et al. | |
| 2017/0138871 A1* | 5/2017 | Li | G01N 24/081 |
| 2017/0356896 A1* | 12/2017 | Anand | G01N 33/2823 |

OTHER PUBLICATIONS

"International Application Serial No. PCT/US2015/063097, Written Opinion dated Sep. 1, 2016" 12 pgs.

* cited by examiner

OIL VISCOSITY PREDICTION

PRIORITY APPLICATIONS

This application is a U.S. National Stage Filing under 35 U.S.C. § 371 from International Application No. PCT/US2015/063097, filed on Dec. 1, 2015, which application is incorporated herein by reference in its entirety.

BACKGROUND

Nuclear magnetic resonance (NMR) logging uses the NMR response of a geological formation surrounding a borehole to determine characteristics of fluids and gases in the formation, providing a continuous record along the length of the borehole. NMR logging exploits the magnetic moment of hydrogen, which is abundant in formation water and hydrocarbons. In many applications, the received NMR signal amplitude is proportional to the quantity of hydrogen nuclei present in the formation.

Generally, NMR tools operate by imposing a static magnetic field on a geological formation. This magnetic field is traditionally referred to as the "main magnetic field" or the "static field" as it is usually independent of time and is given the symbol $B_0$. A second magnetic field, which varies in time, is also applied. This field is typically designated as $B_1$ and is traditionally called the "radio frequency field". It is turned on and off at different times, to create incremental pulses. This second, perturbing field is therefore usually applied perpendicular to the static field, $B_0$. The perturbing field moves the orientation of the magnetization into the transverse (perpendicular) plane.

NMR logging may be used in determining the viscosity of oil. However, complications may arise when trying to determine heavy oil viscosity since the structure and nature of crude oil with heavy components gives rise to fast NMR relaxation.

DETAILED DESCRIPTION

Some of the challenges noted above, as well as others, can be addressed by predicting heavy oil viscosity from wireline and logging while drilling (LWD) logs utilizing NMR echo train data, $T_2$ relaxation distribution data obtained from inversion of echo train data, apparent hydrogen index information, and echo spacing time ($T_E$) information. By obtaining viscosity data and NMR $T_2$ relaxation distribution data on heavy oil samples as a function of $T_E$ and temperature, and performing non-linear regression analysis to model a relationship between the viscosity and NMR $T_2$ geometric mean values, the relationship to $T_E$ can be determined and the viscosity of other oil samples predicted. As used herein, heavy oil may be defined as having a viscosity greater than approximately 100 centipoise (cP).

Figure 1:
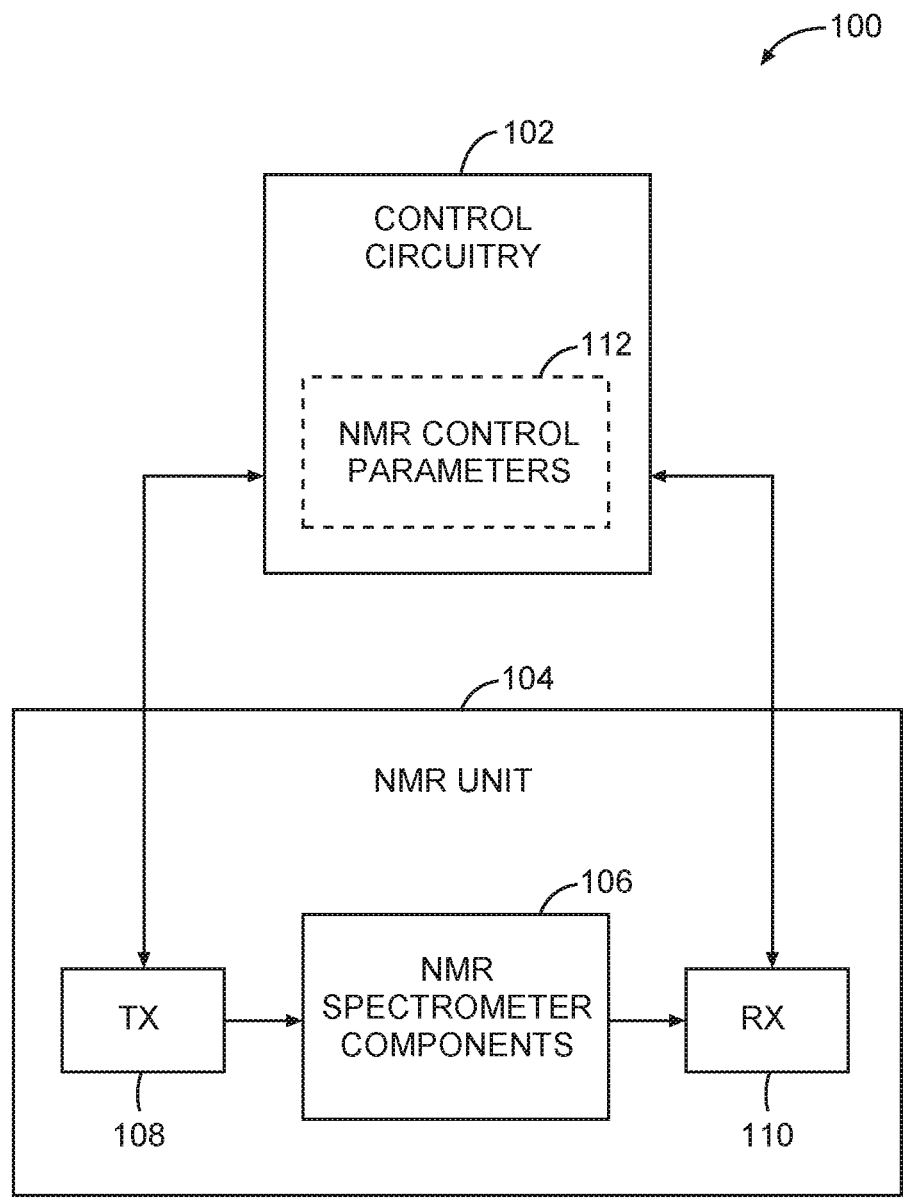
FIG. 1 is a diagram showing an NMR tool, according to various examples of the disclosure.

FIG. 1 is a diagram showing an NMR sensor tool 100, according to various examples of the disclosure. The NMR sensor tool 100 of FIG. 1 is for purposes of illustration only as the various examples disclosed herein may be used in other NMR tools. Fluids, as used herein, may include liquids and/or gases.

The NMR tool 100 includes control circuitry 102 that provides NMR control parameters 112 to an NMR unit 104. In an example, the components of the NMR tool 100 may be located at the surface (e.g., as part of an NMR facility or laboratory) or downhole (e.g., as part of one or more logging tools). In other examples, some of the components (e.g., control circuitry 102) may be located at the surface while other components (e.g., NMR unit 104) are located downhole.

The NMR unit 104 includes a transmitter (TX) 108, a receiver (RX) 110, and NMR spectrometer components 106 for transmitting and receiving NMR signals. The transmitter 108 may include, for example, a programmable pulse sequence device, a radio frequency (RF) synthesizer, a phase shifter, a pulse gate, an amplifier, and/or other components. The receiver 110 may include, for example, an analog-to-digital converter (ADC), filters, mixers, splitters, pre-amplifiers, and/or other components to receive magnetic resonance signals and recover measurement data. The magnetic resonance spectrometer components 106 may include one or more magnets, shim coils, probes/antennas, and/or field-frequency lock components. The magnetic resonance spectrometer components 106 may further include a duplexer that enables separation between transmission current and reception current.

The control circuitry 102 directs the operations of the NMR unit 104 (e.g., forming part of a downhole tool or laboratory equipment) by providing commands, programming, and/or data to transmitter 108 of the magnetic resonance unit 104. Further, in some examples, the magnetic resonance control parameters 112 enable adjustment of pulse sequences and receiver window options based on a default configuration, user selection, and/or calibration.

The transmitter 108 of the NMR unit 104 is configured to transmit signals (e.g., modulated saturation pulses). If the NMR unit 104 is part of a downhole tool, the signals are transmitted outwardly into a geological formation in order to determine relaxation properties of the formation and, as described subsequently, predict a viscosity of heavy oil in the formation.

The receiver 110 of the NMR unit 104 is configured to receive and decode magnetic resonance signals (e.g., from a geological formation). If the NMR unit 104 is part of a downhole tool, the received signals may comprise a reflected response from the geological formation (e.g., reservoir, volume to be measured). The raw NMR measurements or processed NMR data is output from the receiver 110 to the control circuitry 102 for storage, display, and/or analysis. In some embodiments, the control circuitry 102 may further process raw NMR measurements or operate on processed NMR data received from the NMR unit 104.

In NMR logging operations, nuclear magnetic moments are used to measure specific physical and chemical properties of materials. Relaxation of the nuclear spin system is useful for all NMR applications. The relaxation rate depends on the correlation time of molecular motions of the microscopic environment and the strength of the applied magnetic field.

The $T_1$ relaxation time is indicative of the characteristics of the geological formation being measured. For example, different types of formation and different types of fluids may result in different $T_1$ relaxation times during an NMR logging operation.

$T_2$ relaxation affects the decay time of the components of the nuclear spin magnetization perpendicular to $B_0$. In conventional NMR spectroscopy, $T_1$ determines the recycle time, the rate at which an NMR spectrum can be acquired. The transverse (or spin-spin) relaxation time $T_2$ is the decay constant for the component of the nuclear spin magnetization perpendicular to $B_0$. $T_2$ relaxation corresponds to the decoherence of the transverse nuclear spin magnetization. Random fluctuations of the local magnetic field lead to random variations in the instantaneous NMR precession frequency of different spins. As a result, the initial phase coherence of the nuclear spins is lost until eventually the phases are disordered and there is no net xy magnetization. Because $T_2$ relaxation involves only the phases of other nuclear spins it is often referred to in the art as the "spin-spin" relaxation.

NMR relaxometry of fluids may be utilized to predict heavy oil viscosity. This comes from the sensitivity of NMR $T_1$ and $T_2$ relaxation on the molecular motions of the various components of crude oil.

For very light oils or at high temperature conditions, the extreme narrowing approximation is applicable where short correlation times are present due to fast molecular motions that can effectively average out dipole-dipole interactions. In this regime, $T_2$ (spin-spin) and $T_1$ relaxation rates are approximately equal and, by assuming validity of Stokes-Einstein and Debye relationships, the relaxation rates can be related to the viscosity and thermal energy by $$\frac{1}{T_1} = \frac{1}{T_2} \sim \eta / k_B T,$$

where $k_B$ is the Boltzmann constant, and T is the absolute temperature in Kelvin.

For heavy oils, dipole-dipole correlation functions can be described by non-exponential decay giving rise to a power law relationship between NMR $T_2$ relaxation and viscosity as $$\frac{\eta}{T} \sim T_2^{1/\beta},$$

where T is the absolute temperature and $\beta$ is a stretching parameter that determines the width of the spectral density of correlation times.

In conventional NMR viscosity correlations, $\beta=1$ for single or unique correlation times due to random motion, which is applicable for light oils or very high temperature scenarios. For multi-component fluid systems such as heavy oils, this is not usually desirable.

In heavy oils, a distribution of different environments may exist and non-Debye relaxation may be more relevant where motions are inherently non-random. This may lead to correlated motion that gives rise to relaxation. The order parameter $\beta$ is directly related to the width of the spectral density and, thus, the degree of correlation motion. The stretching parameter $\beta=1$ implies a single activation energy as expected with uncorrelated motion whereas $\beta=0$ assumes the maximum distribution of activation energies or correlation times.

Various embodiments make use of a power law functional dependence for the NMR viscosity correlation, and use the echo spacing time ($T_E$) as another experimental parameter within the equation. Thus, $T_E$ is not only used for the relaxation behavior of heavy oils probed by NMR $T_2$ relaxation but also for the application in logging situations where constraints on $T_E$ exist. Therefore, the $T_2$ distribution deficit can be corrected at relatively larger echo spacings as illustrated in FIG. 2.

Figure 2:
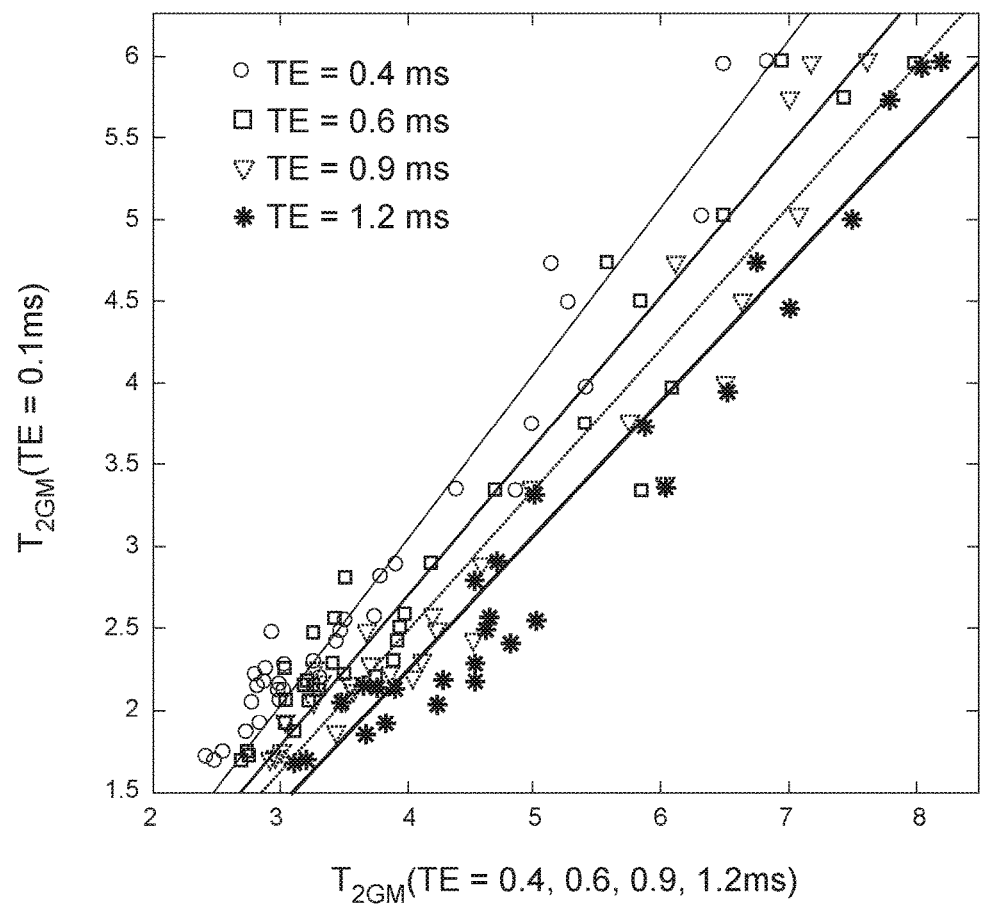
FIG. 2 is a plot showing the dependence of $T_2$ geometric mean at various echo times, according to various examples of the disclosure.

FIG. 2 is a plot showing the dependence of $T_2$ geometric mean at various echo times, according to various examples of the disclosure. This figure illustrates a summary of the dependence of $T_2$ geometric mean ($T_{2GM}$) for $T_E=0.1$ millisecond (ms) on $T_{2GM}$ for $T_E$ of various echo spacing times (e.g., 0.4 ms, 0.6 ms, 0.9 ms, 1.2 ms).

Assuming that the $T_2$ geometric mean at $T_E=0.1$ ms is most representative of intrinsic relaxation time or a value close to the intrinsic relaxation time, FIG. 2 shows the systematic shift of the geometric mean of $T_2$ relaxation as $T_E$ increases. A seemingly linear relationship is exhibited that may be expressed as: $T_{2GM,intrinsic}=T_{2GM,TE}+aT_E+b$, where a and b are fitting parameters.

Since the NMR relaxation signals are TE dependent, the relationship between $\beta$ and $T_E$ is considered in the power law correlation between viscosity and the NMR $T_2$ relaxation described above.

Figure 3:
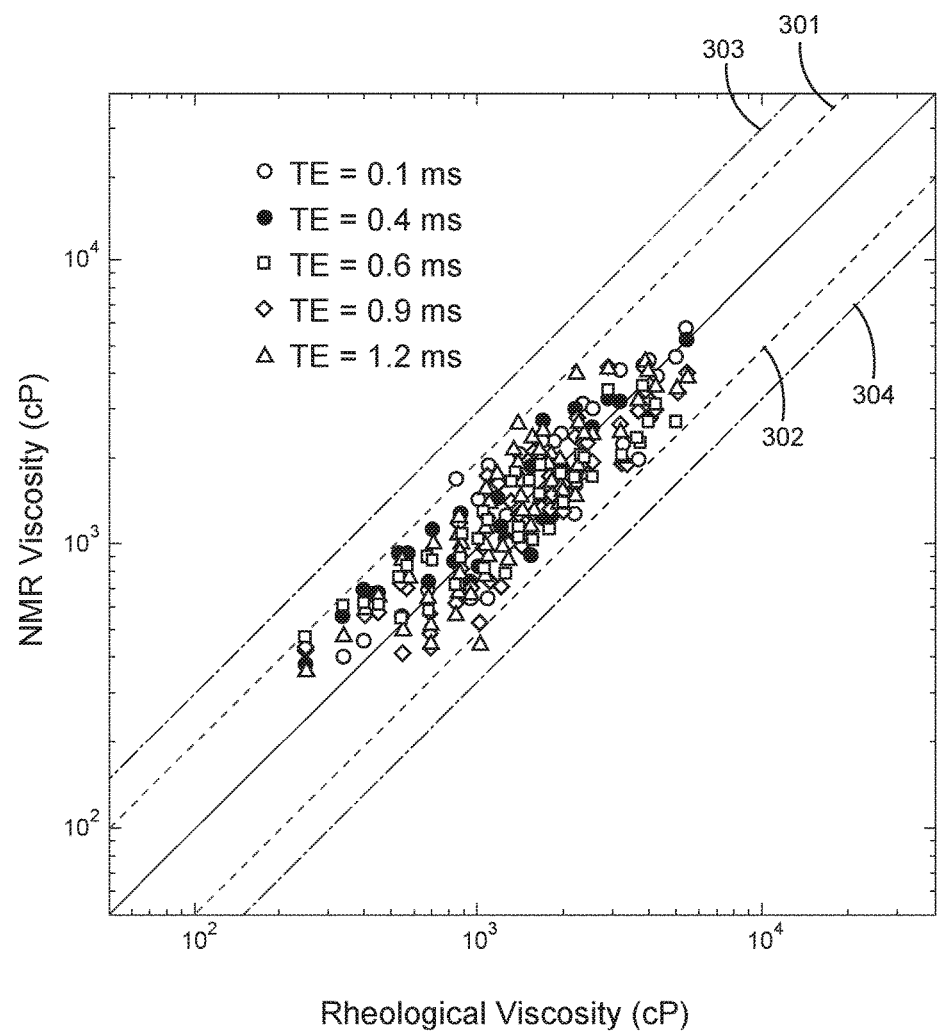
FIG. 3 is a plot showing how rheological viscosity compares to an NMR predicted viscosity based on a first correlation, according to various examples of the disclosure.

FIG. 3 is a plot showing how rheological viscosity compares to an NMR predicted viscosity based on a first correlation, according to various examples of the disclosure. The rheological viscosity (in cP) is along the x-axis and the NMR viscosity (in cP) is along the y-axis.

This figure demonstrates how the rheological viscosity compares to the NMR predicted viscosity of dead oil (oil without dissolved gas) by utilizing $T_E$ as an additional input parameter. The illustrated example uses $T_E$ of 0.1, 0.4, 0.6, 0.9, and 1.2 ms. Other echo times are possible. The example illustrated in FIG. 3 uses a first correlation of:

$$\frac{\eta}{T} \sim \left(\frac{1}{T_{2GM} + cTE + d}\right)^{1/(-aTE+b)},$$

where $T_{2GM}$ is the $T_2$ geometric mean and a, b, c, and d are fitting constants. $T_{2GM}$ and the power coefficient are both linearly related to $T_E$.

Figure 4:
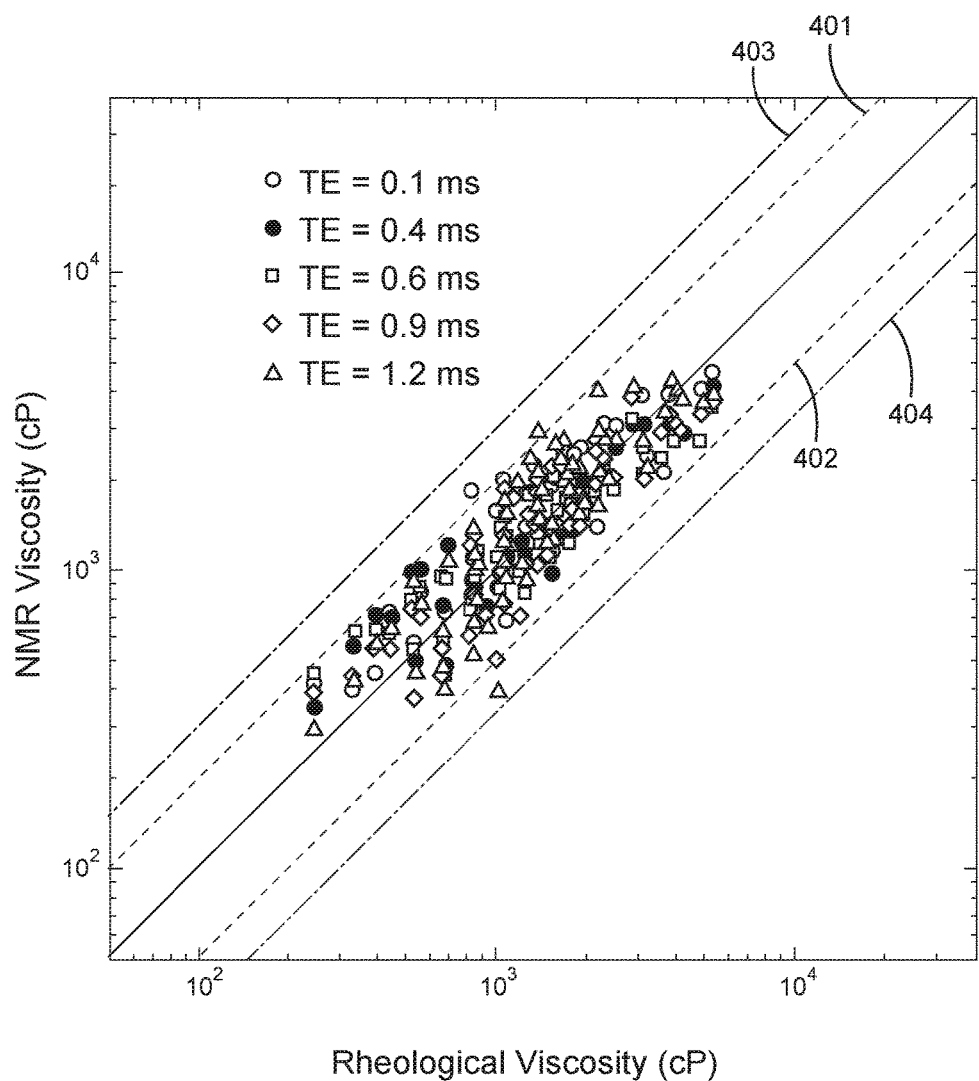
FIG. 4 is a plot showing how rheological viscosity compares to an NMR predicted viscosity based on a second correlation, according to various examples of the disclosure.

FIG. 4 is a plot showing how rheological viscosity compares to an NMR predicted viscosity based on a second correlation, according to various examples of the disclosure. The rheological viscosity (in centipoise (cP)) is along the x-axis and the NMR viscosity (in cP) is along the y-axis. This figure demonstrates how the rheological viscosity compares to the NMR predicted viscosity of dead oil by utilizing $T_E$ as an additional input parameter. The illustrated example uses $T_E$ of 0.1, 0.4, 0.6, 0.9, and 1.2 ms. Other echo times are possible.

The example of FIG. 4 uses a second correlation of $$\frac{\eta}{T} \sim \left(\frac{1}{T_{2GM}}\right)^{1/(-eTE+f)},$$

where $T_{2GM}$ is the $T_2$ geometric mean and a, b, c, d, e, and f are fit parameters. The expression $$\frac{\eta}{T} \sim \left(\frac{1}{T_{2GM}}\right)^{1/(-eT_E+f)}$$

can be derived from considering the ratio:

$$r(T_E) = \left(\frac{\frac{1}{T_{2GM} + cT_E + d}}{\frac{1}{T_{2GM}}}\right)$$

of the right-hand sides of the correlation functions. This can be re-expressed as $$\left(\frac{1}{T_{2GM} + cT_E + d}\right)^{1/(-aT_E+b)} = \left(\frac{1}{T_{2GM}}\right)^{1/(-aT_E+b)} (r(T_E))^{1/(-aT_E+b)} = \left(\frac{1}{T_{2GM}}\right)^{1/(-eT_E+f)}.$$

The fitting coefficients e and f come from absorbing the ratio function.

Figure 5:
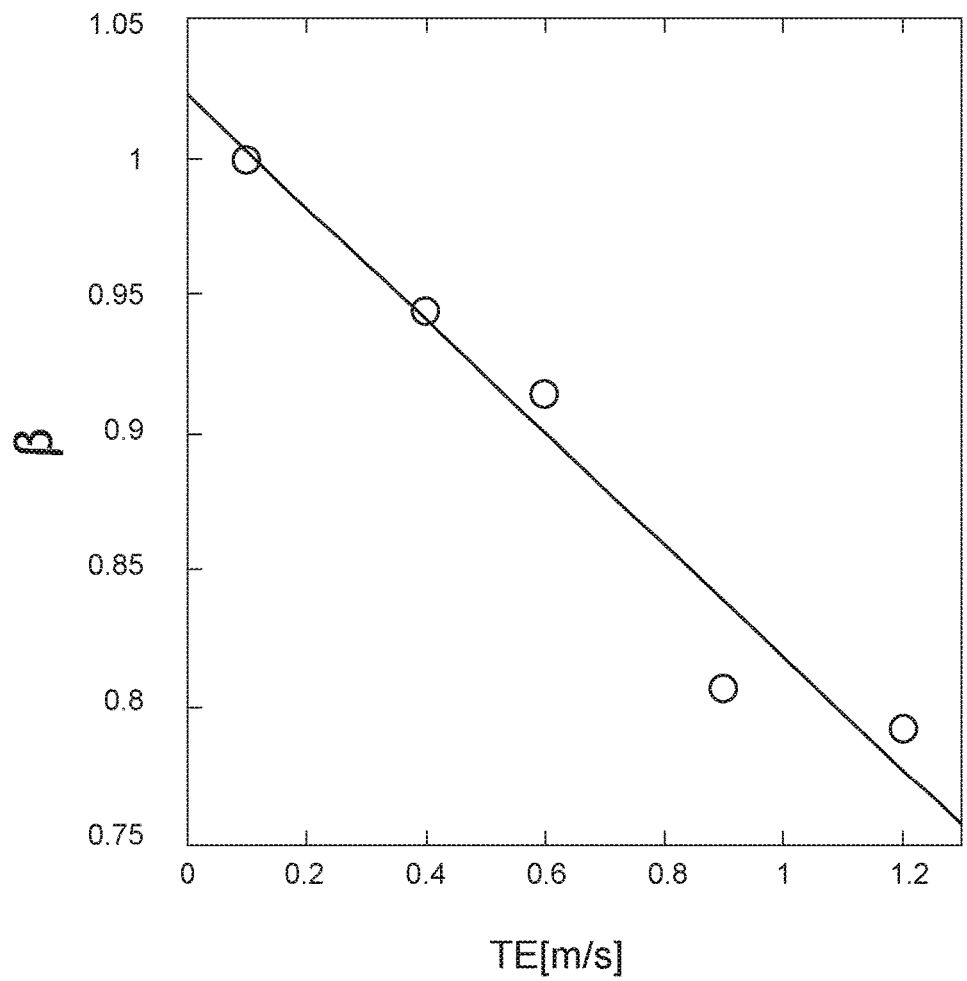
FIG. 5 is a plot showing a linear relationship of a power coefficient, according to various examples of the disclosure.

The power law coefficient, $1/(aT_E+b)$, may be rewritten as $1/\beta$, where $0 \le \beta \le 1$ and varies linearly with $T_E$, as demonstrated by the plot of FIG. 5. The long dashed lines 301, 302, 401, 402 and long/short dashed lines 303, 304, 403, 404 in each of the FIGS. 3 and 4 plots correspond to NMR predicted viscosities that fall within a factor of 2 and 3 of the rheological viscosities, respectively. Both the first and second correlations demonstrate reasonable predictions of viscosity at a specified $T_E$.

The $R^2$ values are 0.8 and 0.7 for FIGS. 3 and 4, respectively. This implies that using $T_E$ to correct for the deficit in the $T_{2GM}$ and power coefficient may result in a more reliable viscosity prediction.

FIG. 5 is a plot showing a linear relationship of a power coefficient, according to various examples of the disclosure. The echo spacing time $T_E$ (in ms) is along the x-axis and the stretching parameter, $\beta$, (determines the width of the spectral density of correlation times) is along the y-axis. This plot illustrates how $\beta$ varies linearly with echo spacing times $T_E$.

Figure 6:
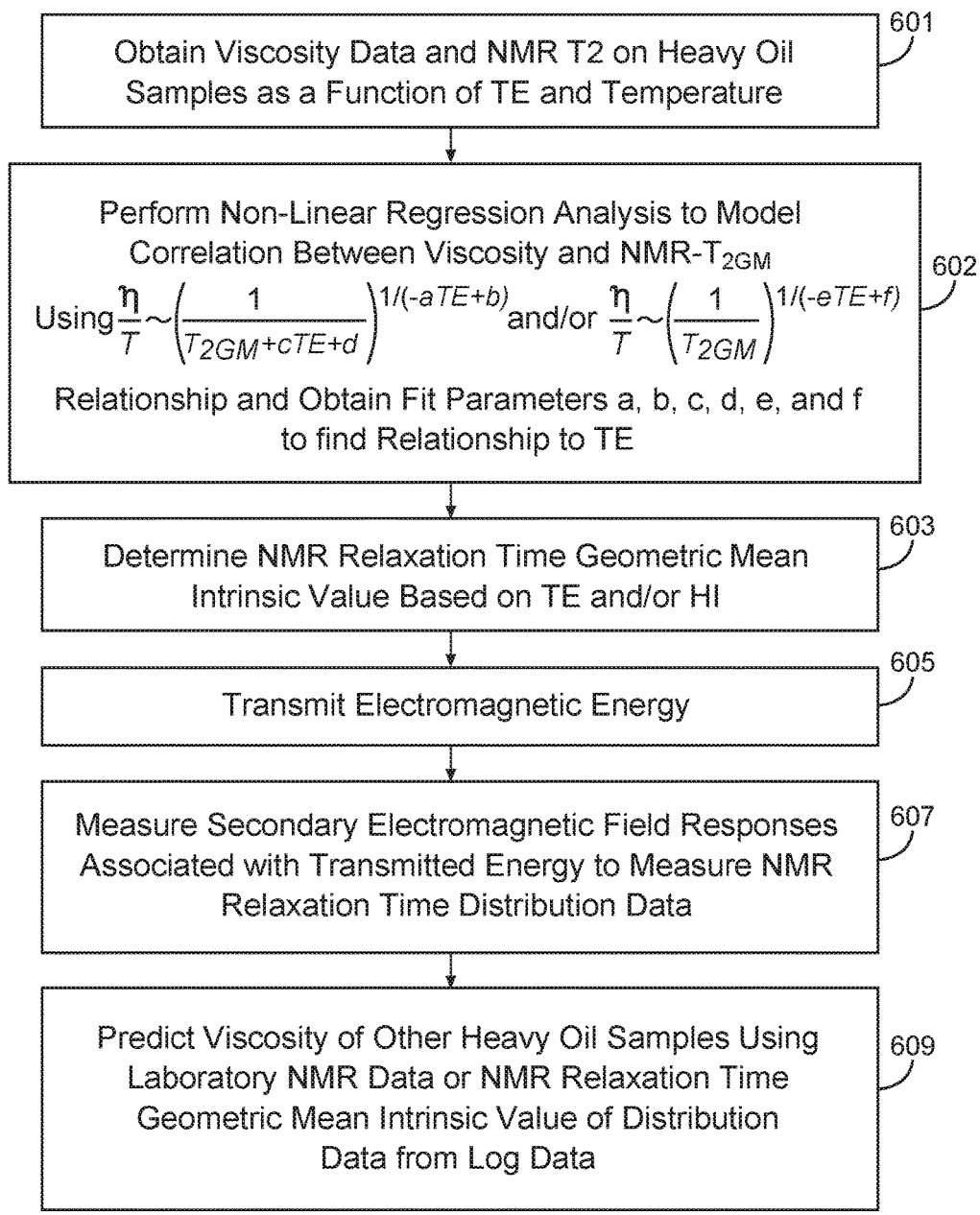
FIG. 6 is a flowchart of a method for heavy oil viscosity predictions, according to various examples of the disclosure.

FIG. 6 is a flowchart of a method for heavy oil viscosity predictions, according to various examples of the disclosure. This flowchart illustrates an example of a workflow for using a viscosity correlation for predicting viscosity of oil within a lab or logging environment (e.g., measurement while drilling/logging while drilling (MWD/LWD), wireline). The method uses the echo train data, T2 distribution data from inversion of echo train data, $T_{2GM}$ computed from the distributions, and $T_E$ parameters as described previously.

In block 601, the viscosity data, NMR $T_2$ echo train data, and relaxation time distribution data (e.g., $T_1$ and/or $T_2$) from inversion of echo train data are obtained for a set of oil samples as a function of $T_E$ and temperature. In an example, the viscosity data may include parameters such as temperature range of the oil sample, the heating or cooling rate of the sample, and/or the rotational frequency of the parallel plates (e.g., in Hertz). These experimental parameters are first optimized and used to ensure a more accurate measurement of viscosity and are not used in developing a model. The NMR $T_2$ data may be obtained by measuring the $T_2$ relaxation as a function of temperature and $T_E$.

In block 602, a non-linear regression analysis is performed in order to model the correlation between viscosity and NMR relaxation time geometric mean (e.g., $T_{2GM}$) for the set of oil samples. The modeling results in generating the fit parameters a, b, c, d, e, and f. The fit parameters may be defined as fitting coefficients that define the correlation of the viscosity with temperature.

The modeling may be accomplished using the first and/or the second correlation functions:

$$\frac{\eta}{T} \sim \left(\frac{1}{T_{2GM} + cT_E + d}\right)^{1/(-aT_E+b)} \text{ and/or}$$

$$\frac{\eta}{T} \sim \left(\frac{1}{T_{2GM}}\right)^{1/(-eT_E+f)}.$$

This modeling determines the relationship of the viscosity to $T_E$.

Once the relationship of the oil viscosity is determined with respect to $T_E$ and temperature, the intrinsic $T_{2GM}$ ($T_{2GM\_intrinsic}$) value or a value as close as possible to the intrinsic $T_{2GM}$ can be solved, in block 603, by the approximation:

$$\left(\frac{1}{T_{2GM} + cT_E + d}\right)^{1/(-aT_E+b)} \sim \left(\frac{1}{T_{2GM\_intrinsic}}\right)^{1/(-aT_E+b)},$$

where $T_{2GM\_intrinsic} = T_{2GM} + cTE + d$. This can also be determined from $$\left(\frac{1}{T_{2GM}}\right)^{1/(-eT_E+f)} \sim \left(\frac{1}{T_{2GM\_intrinsic}}\right)^{1/(-aT_E+b)},$$

where $T_{2GM\_intrinsic} = (T_{2GM})^{(-eT_E+f)/(-aT_E+b)}$.

Based on the relationship of the oil viscosity with respect to $T_E$ and temperature, the viscosity of other oil samples may be determined. In an example, this may be accomplished downhole by transmitting electromagnetic energy (e.g., NMR pulse(s)) at one or more frequencies, in block 605. The NMR pulse(s) may be transmitted into a geological formation comprising a hydrocarbon reservoir.

In block 607, secondary electromagnetic field responses, associated with the electromagnetic energy, are measured. The secondary electromagnetic field responses provide indications of NMR relaxation time distribution data measurements. These responses (e.g., log data) may be returns from the hydrocarbon reservoirs in the geological formation. The viscosity of the heavy oil in the hydrocarbon reservoir may then be determined, in block 609, based on the correlation between the set of viscosity data and the NMR relaxation time geometric mean value for the distribution data (e.g., from log data). In another example, NMR data from experimentation may be used to determine the viscosity.

In some examples of heavy oil viscosity determination, a hydrogen index may be used in estimating the heavy oil viscosity, as described subsequently. The hydrogen index is defined as the density of hydrogen relative to that of water, as described subsequently.

The geometric mean of $T_2$ ($T_{2GM}$) may be calculated from the "binned porosity" (i.e., $T_2$ distribution into bins or groups of similar values), obtained from an inversion of measured magnetization decay:

$$\ln(T_{2GM}) = \frac{\sum_i^n \phi_i \ln(T_2^i)}{\sum_i^n \phi_i} \qquad (1)$$

where $\phi_i$ is the binned porosity for a specified relaxation time $T_2^i$.

The hydrogen index (HI) is defined as follows $$HI = \frac{\text{Amount of hydrogen in sample of a unit volume}}{\text{Amount of hydrogen in pure water of a unit volume at } STP}. \qquad (2)$$

An amplitude of the response of the NMR logging tool is calibrated with respect to that of bulk water at standard conditions. The HI of a fluid sample can then be expressed as:

$$HI = \frac{\sum_i^n \phi_i}{\phi(1 - S_w - S_g)} \qquad (3)$$

Theoretically, the HI of the hydrocarbon fluid is close to 1. However, due to the limitations of NMR acquisition hardware, the components of $T_2$ that are less than the echo spacing may be lost. Thus the measured HI values are less than the actual values (i.e., 1), especially in a heavy oil example. HI loss is a function of $T_E$ and the $T_2$ components less than $T_E$. The larger the HI loss, the longer the $T_E$. The loss of short $T_2$ components may also induce the calculated $T_{2GM}$ to deviate from the true $T_{2GM}$ of the heavy oil.

Therefore, a more accurate estimate of $T_{2GM}$, at any echo spacing, may be expressed as:

$$\ln(T_{GM-intrinsic}) = HI \cdot \ln(T_{2GM}) + (1-HI) \cdot \ln(f(0 \leq t \leq T_E)), \qquad (4)$$

where $f(0 \leq t \leq TE)$ is a function that relates the $T_2$ distribution at the time t that is less than the echo time during NMR acquisition.

The role of the first term (i.e., $HI \cdot \ln(T_{2GM})$) on the right side of Eqn. (4) is to reduce $T_{2GM}$ when it is over-weighted and the role of the second term (i.e., $(1-HI) \cdot \ln(f(0 \leq t \leq T_E))$) is to recover $T_{2GM}$ where it is missing. That is, HI provides a way to weight the NMR data (e.g., experimentation data). This results in a more accurate estimate of $T_{2GM}$ over the range of $T_2$ spectrum.

The more accurate estimated $T_{2GM}$ is correlated with the heavy oil viscosity in the power law function as:

$$\ln\left(\frac{\eta}{T}\right) = -a \ln(T_{2GM-intrinsic}) + b \qquad (5)$$

or $$\frac{\eta}{T} = b'(T_{2GM-intrinsic})^{-a'}.$$

Figure 7:
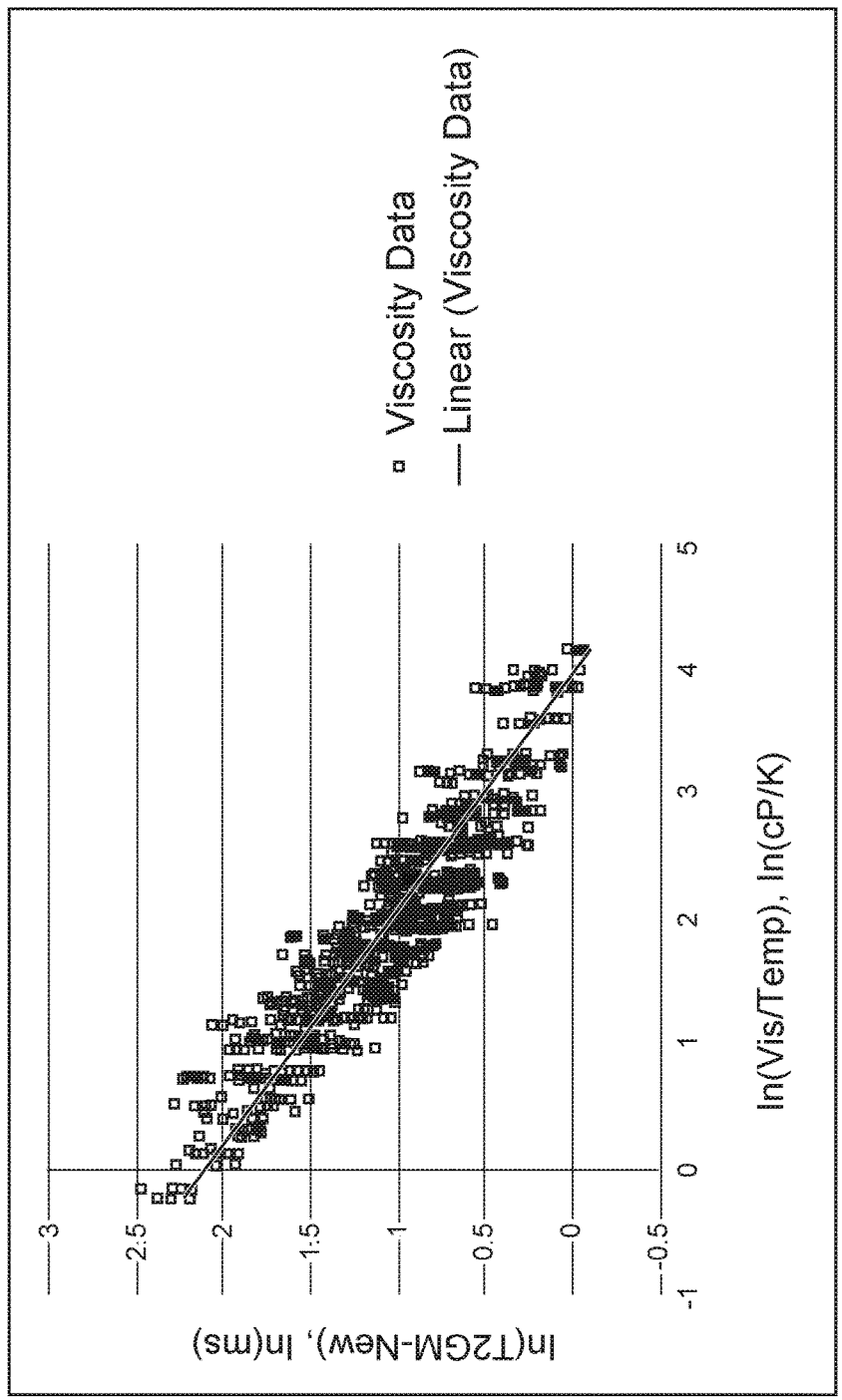
FIG. 7 is a plot showing a power law relationship between $T_2$ geometric mean and heavy oil viscosity, according to various examples of the disclosure.

FIG. 7 is a plot showing a power law relationship between $T_2$ geometric mean and heavy oil viscosity, according to various examples of the disclosure. The ln(Viscosity/Temperature), ln(cP/K) is along the x-axis and the ln($T_{2GM-new}$), ln(ms) is along the y-axis. This figure shows a linear relationship between the viscosity data and the $T_{2GM-new}$ data.

Figure 8:
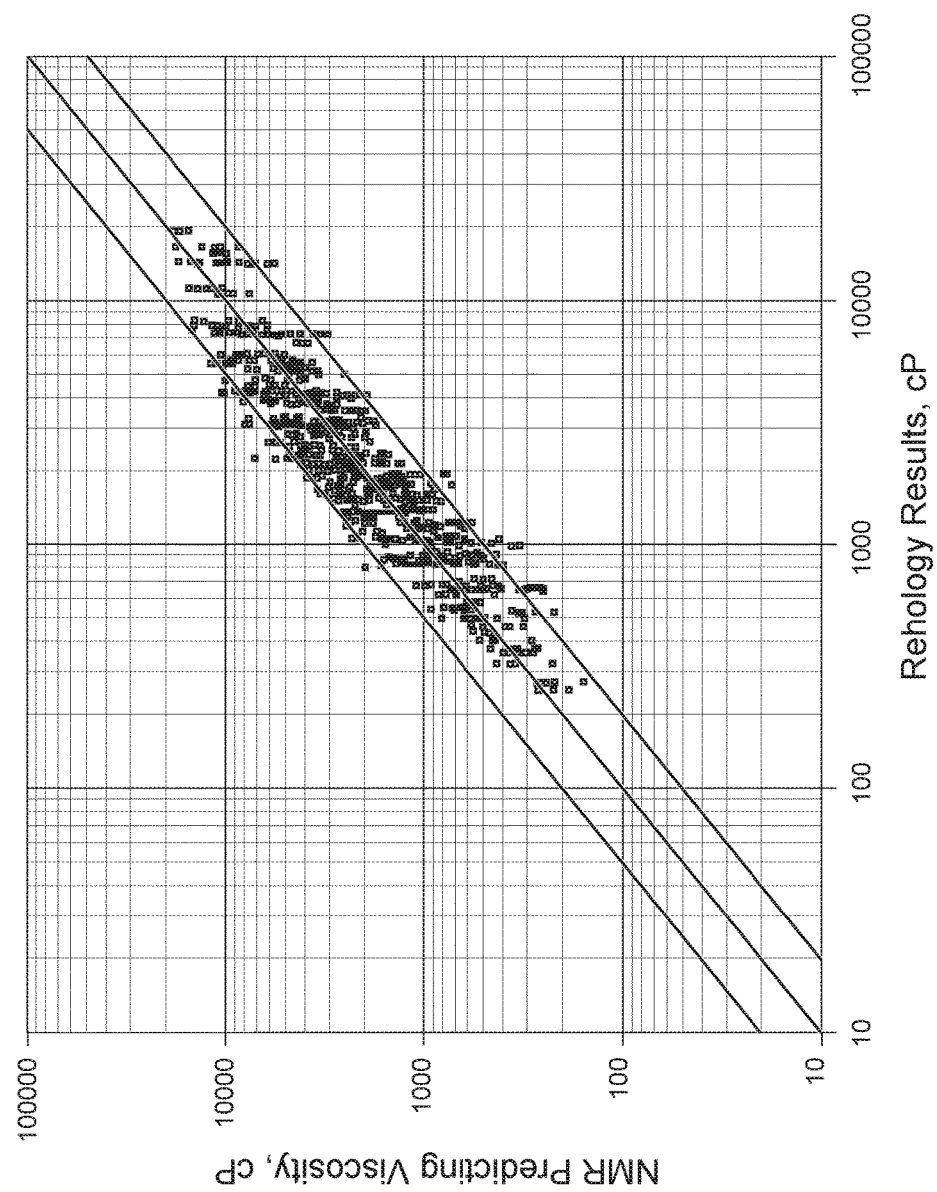
FIG. 8 is a plot showing a comparison between rheological viscosity and NMR predicted viscosity, according to various examples of the disclosure.

FIG. 8 is a plot showing a comparison between rheological viscosity and NMR predicted viscosity, according to various examples of the disclosure. The rheology results (in cP) are along the x-axis and the NMR predicted viscosity (in cP) are along the y-axis. This figure shows the results of the plotting of data from Eqn. (5).

Figure 9:
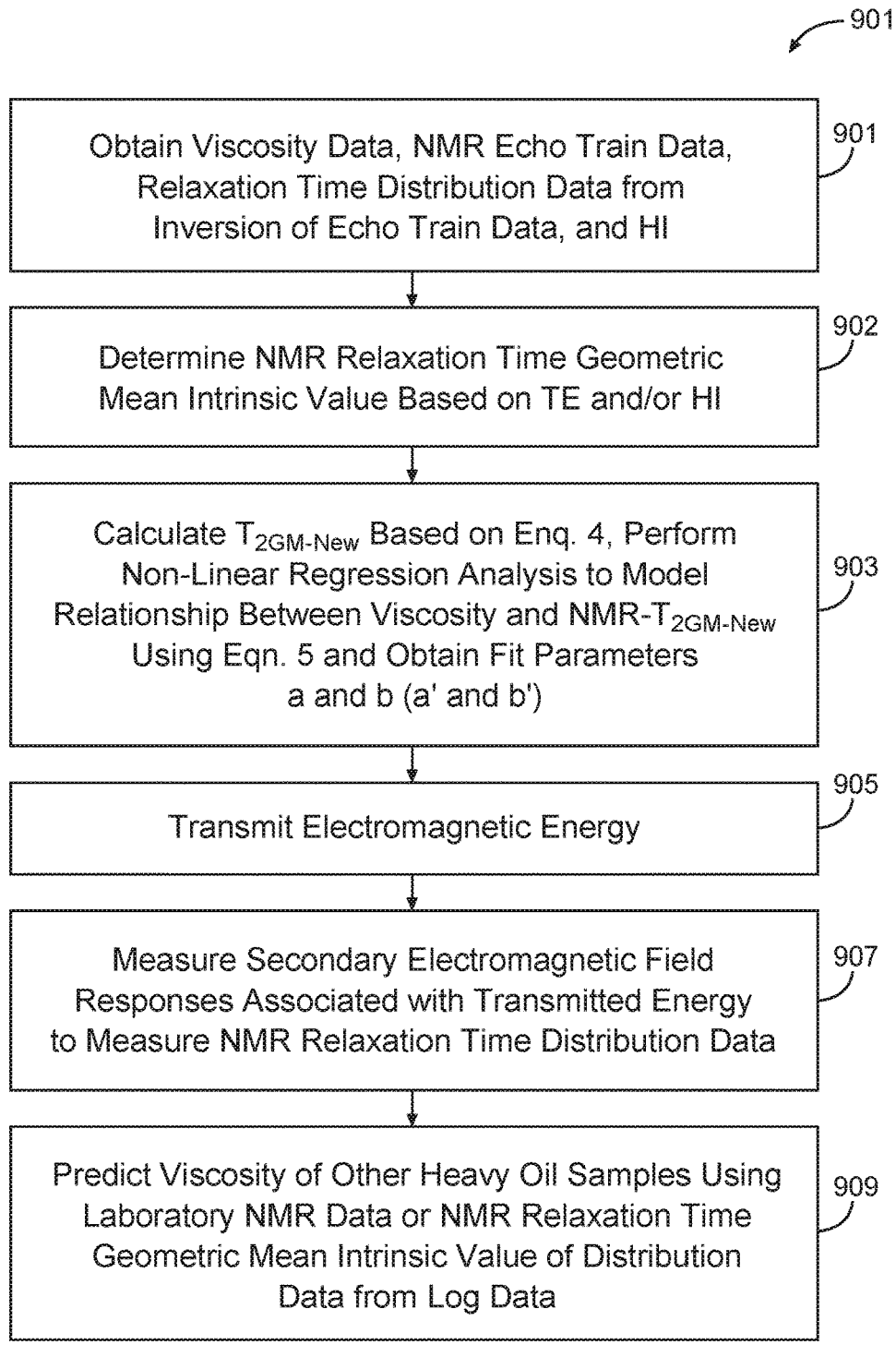
FIG. 9 is a flowchart of a method for heavy oil viscosity predictions using a hydrogen index, according to various examples of the disclosure.

FIG. 9 is a flowchart of a method for heavy oil viscosity predictions using a hydrogen index, according to various examples of the disclosure. In block 901, the viscosity data, NMR echo train data, relaxation time distribution data (e.g., $T_1$ and/or $T_2$) from inversion of echo train data, and hydrogen index for a set of heavy oil samples are obtained. In an example, the viscosity data acquisition may include parameters such as temperature range of the oil sample, the heating or cooling rate of the sample, and/or the rotational frequency of the parallel plates (e.g., in Hertz). These experimental parameters are used to ensure a more accurate measurement of viscosity and are not used in developing a model. The NMR $T_2$ data may be obtained by measuring the $T_2$ relaxation as a function of temperature and $T_E$. The hydrogen index may be calculated using the above Eqn. (2).

In block 902, an NMR relaxation time geometric mean intrinsic value or a value close to it is determined based on the HI and/or TE by using $\ln(T_{2GM\_intrinsic}) = HI \cdot \ln(T_{2GM}) + (1-HI) \cdot \ln(f(0 \leq t \leq T_E))$.

In block 903, the NMR $T_{2GM\text{-}intrinsic}$ is calculated based on Eqn. (4) above and a non-linear regression analysis is performed to model the relationship between the viscosity of the oil sample and the NMR $T_{2GM\text{-}intrinsic}$ using one of Eqn. (5) above. The modeling results in the fit parameters (a and b) or (a' and b') depending on which power law function is used. Alternately, once the model is determined based on the fit coefficients, one can use viscosity and temperature to predict an NMR relaxation time geometric mean value.

Once the relationship of the oil viscosity is determined with respect to NMR $T_{2GM\text{-}intrinsic}$, the viscosity of other oil samples may be determined. In an example, this may be accomplished downhole by transmitting electromagnetic energy (e.g., NMR pulse(s)) at one or more frequencies, in block 905. The NMR pulse(s) may be transmitted into a geological formation comprising a hydrocarbon reservoir.

In block 907, secondary electromagnetic field responses, associated with the electromagnetic energy, are measured. The secondary responses provide an indication of the NMR relaxation time distribution data from the oil in the formation. These responses (e.g., log data) may be returns from the hydrocarbon reservoirs in the geological formation. The viscosity of the heavy oil in the hydrocarbon reservoir may then be determined, in block 909, based on the correlation between the set of viscosity data and the NMR relaxation time geometric mean intrinsic value of the distribution data (e.g., log data). In another example, NMR data from experimentation may be used to determine the viscosity.

Figure 10:
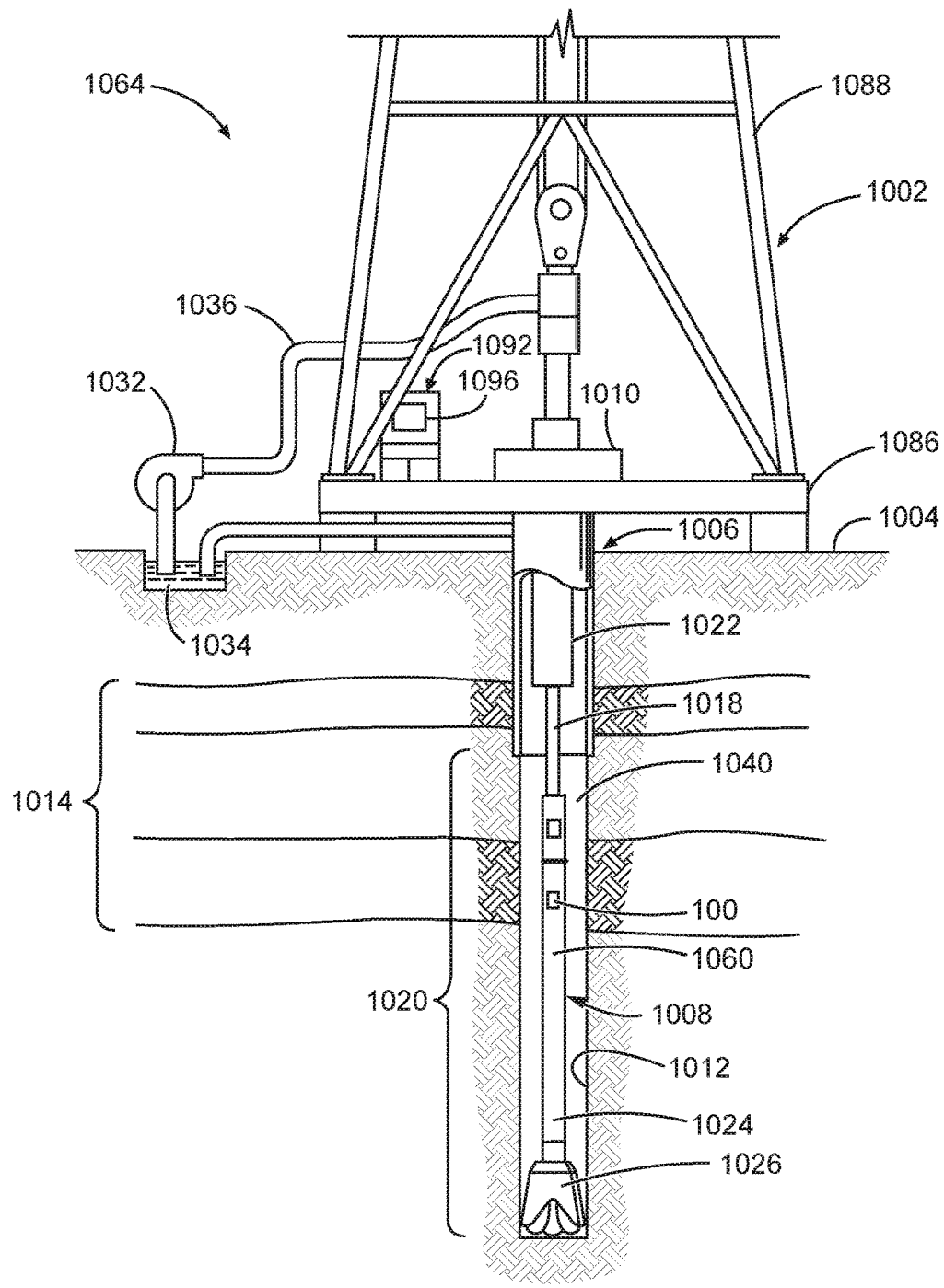
FIG. 10 is a diagram showing a drilling system, according to various examples of the disclosure.

FIG. 10 is a diagram showing a drilling system 1064, according to various examples of the disclosure. The system 1064 includes a drilling rig 1002 located at the surface 1004 of a well 1006. The drilling rig 1002 may provide support for a drillstring 1008. The drillstring 1008 may operate to penetrate the rotary table 1010 for drilling the borehole 1012 through the subsurface formations 1014. The drillstring 1008 may include a drill pipe 1018 and a bottom hole assembly (BHA) 1020 (e.g., drill string), perhaps located at the lower portion of the drill pipe 1018.

The BHA 1020 may include a MWD/LWD tool 1060, including the NMR tool 100 described previously, and a drill bit 1026. The drill bit 1026 may operate to create the borehole 1012 by penetrating the surface 1004 and the subsurface formations 1014.

The NMR tool 100 may be used to determine and predict a viscosity of oil in the subsurface formation during a logging operation. For example, the methods of FIG. 6 and/or FIG. 9 may be used in determining and predicting the viscosity.

During drilling operations within the borehole 1012, the drillstring 1008 (perhaps including the drill pipe 1018 and the BHA 1020) may be rotated by the rotary table 1010 and/or by the mud motor 1090 that is located down hole. The drill collars 1022 may be used to add weight to the drill bit 1026. Drill collars 1022 may also operate to stiffen the BHA 1020, allowing the BHA 1020 to transfer the added weight to the drill bit 1026, and in turn, to assist the drill bit 1026 in penetrating the surface 1004 and subsurface formations 1014.

During drilling operations within the borehole 1012, a mud pump 1032 may pump drilling fluid (sometimes referred to as "drilling mud") from a mud pit 1034 through a hose 1036 into the drill pipe 1018 and down to the drill bit 1026. The drilling fluid can flow out from the drill bit 1026 and be returned to the surface 1004 through an annular area 1040 between the drill pipe 1018 and the sides of the borehole 1012. The drilling fluid may then be returned to the mud pit 1034, where such fluid is filtered. In some examples, the drilling fluid can be used to cool the drill bit 1026, as well as to provide lubrication for the drill bit 1026 during drilling operations. Additionally, the drilling fluid may be used to remove subsurface formation cuttings created by operating the drill bit 1026.

A workstation 1092 including a controller 1096 may include modules comprising hardware circuitry, a processor, and/or memory circuits that may store software program modules and objects, and/or firmware, and combinations thereof that are configured to execute the above-described methods of FIGS. 6 and 9 as instructions.

In an example, the NMR tool 100 may be used to transmit an electromagnetic field and then measure the resulting secondary electromagnetic field responses generated by the formation 1014. The resulting data may be transmitted to the surface workstation 1092 via telemetry. The workstation 1092, with its controller 1096, may process that telemetry, execute any methods disclosed herein, and determine and predict a viscosity of oil in the formation 1014.

Figure 11:
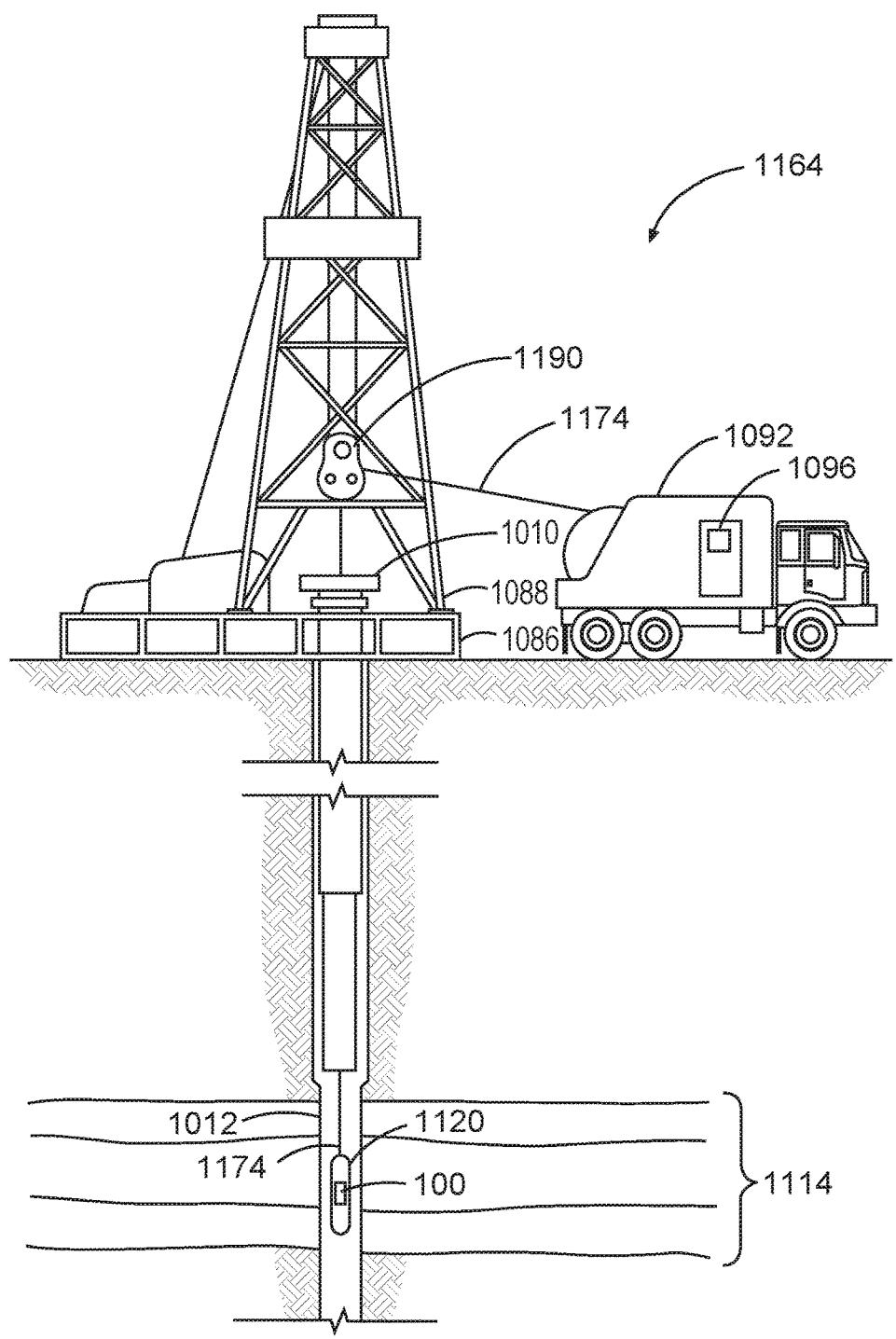
FIG. 11 is a diagram showing a wireline system, according to various examples of the disclosure.

FIG. 11 is a diagram showing a wireline system 1164, according to various examples of the disclosure. The system 1164 may comprise at least one wireline logging tool body 1120, as part of a wireline logging operation in a borehole 1112, including the NMR tool 100 as described previously.

A drilling platform 1186 equipped with a derrick 1188 that supports a hoist 1190 can be seen. Drilling oil and gas wells is commonly carried out using a string of drill pipes connected together so as to form a drillstring that is lowered through a rotary table 1110 into the borehole 1112. Here it is assumed that the drillstring has been temporarily removed from the borehole 1112 to allow the wireline logging tool body 1120, such as a probe or sonde with the NMR tool 100, to be lowered by wireline or logging cable 1174 (e.g., slickline cable) into the borehole 1112. Typically, the wireline logging tool body 1120 is lowered to the bottom of the region of interest and subsequently pulled upward at a substantially constant speed.

During the upward trip, at a series of depths, the NMR tool 100 may be used to determine the characteristics of the formation 1114 or a reservoir in the formation 1114. The resulting data may be communicated to a surface logging facility (e.g., workstation 1092) for processing, analysis, and/or storage. The workstation 1092 may have a controller 1096 that is able to execute any methods disclosed herein.

Figure 12:
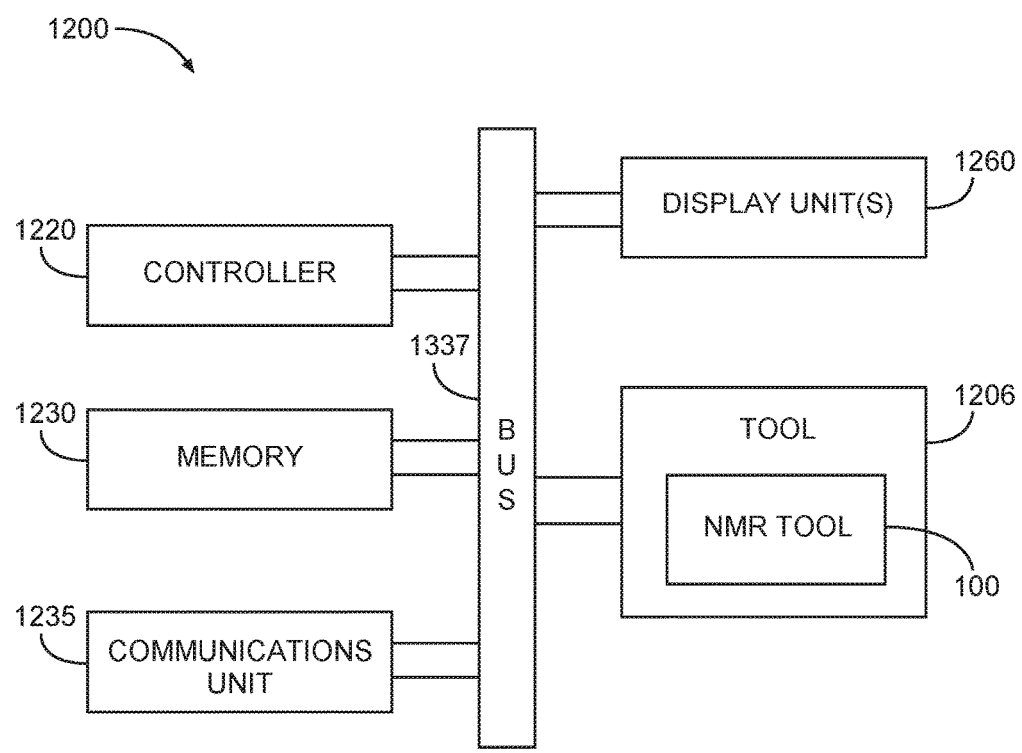
FIG. 12 is a block diagram of an example system operable to implement the activities of multiple methods, according to various examples of the disclosure.

FIG. 12 is a block diagram of an example system 1200 operable to implement the activities of multiple methods, according to various examples of the disclosure. The system 1200 may include a tool housing 1206 having the NMR tool 100 disposed therein. The system 1200 may be implemented as shown in FIGS. 10 and 11 with reference to the workstation 1092 and controller 1096.

The system 1200 may include circuitry such as a controller 220, a memory 1230, and a communications unit 1235. The memory 1230 may be structured to include a database. The controller 1220, the memory 1230, and the communications unit 1235 may be arranged to operate as control circuitry to control operation of the NMR tool 100 and execute any methods disclosed herein in order to determine the characteristics of a fluid and/or formation.

The communications unit 1235 may include communications capability for communicating from downhole to the surface or from the surface to downhole. Such communications capability can include a telemetry system such as mud pulse telemetry. In another example, the communications unit 1235 may use combinations of wired communication technologies and wireless technologies.

The system 1200 may also include a bus 1237 that provides electrical conductivity among the components of the system 1200. The bus 1237 can include an address bus, a data bus, and a control bus, each independently configured or in an integrated format. The bus 1237 may be realized using a number of different communication mediums that allows for the distribution of components of the system 1200. The bus 1237 may include a network. Use of the bus 1237 may be regulated by the controller 1220.

The system 1200 may include display unit(s) 1260 as a distributed component on the surface of a wellbore, which may be used with instructions stored in the memory 1230 to implement a user interface to monitor the operation of the tool 1206 or components distributed within the system 1200. The user interface may be used to input parameter values for thresholds such that the system 1200 can operate autonomously substantially without user intervention in a variety of applications. The user interface may also provide for manual override and change of control of the system 1200 to a user. Such a user interface may be operated in conjunction with the communications unit 1235 and the bus 1237.

These implementations can include a machine-readable storage device having machine-executable instructions, such as a computer-readable storage device having computer-executable instructions. Further, a computer-readable storage device may be a physical device that stores data represented by a physical structure within the device. Such a physical device is a non-transitory device. Examples of machine-readable storage devices can include, but are not limited to, read only memory (ROM), random access memory (RAM), a magnetic disk storage device, an optical storage device, a flash memory, and other electronic, magnetic, and/or optical memory devices.

Example 1 is a method, comprising: transmitting electromagnetic energy into a formation; measuring NMR relaxation time distribution data for oil in the formation based on secondary electromagnetic field responses associated with the electromagnetic energy; and determining a viscosity of the oil in the formation based on a correlation between a set of viscosity data and an NMR relaxation time geometric mean intrinsic value of distribution data derived from an echo spacing time (TE) and/or a hydrogen index (HI).

In Example 2, the subject matter of Example 1 can further include obtaining the set of viscosity data and nuclear magnetic resonance (NMR) relaxation time distribution data for a plurality of oil samples; determining the NMR relaxation time geometric mean intrinsic value for the distribution data; and determining the correlation between the set of viscosity and the NMR relaxation time geometric mean for the NMR relaxation time distribution data.

In Example 3, the subject matter of Examples 1-2 can further include: obtaining hydrogen indexes for the plurality of oil samples; performing a non-linear regression analysis to model the correlation between the set of viscosity data and the NMR relaxation time geometric mean intrinsic value; and obtaining fit parameters based on the non-linear regression analysis.

In Example 4, the subject matter of Examples 1-3 can further include: obtaining the viscosity data and the NMR relaxation time distribution as a function of echo spacing time and temperature of the oil sample; and performing a non-linear regression analysis and obtaining fit parameters to model the correlation between the set of viscosity data and the NMR relaxation time geometric mean as a function of the echo spacing time.

In Example 5, the subject matter of Examples 1-4 can further include using one or more correlation functions to model the correlation between the set of viscosity data and the NMR relaxation time geometric mean intrinsic value.

In Example 6, the subject matter of Examples 1-5 can further include wherein the one or more correlation functions comprise:

$$\frac{\eta}{T} \sim \left(\frac{1}{T_{2GM} + cT_E + d}\right)^{1/(-aT_E+b)} \text{ and/or}$$

$$\frac{\eta}{T} \sim \left(\frac{1}{T_{2GM}}\right)^{1/(-eT_E+f)},$$

where η is viscosity of an oil sample, T is a temperature of the oil sample, $T_{2GM}$ is the NMR relaxation time geometric mean for the oil sample, $T_E$ is the echo spacing time, and a, b, c, d, e and f are the fit parameters.

In Example 7, the subject matter of Examples 1-6 can further include wherein the one or more correlation functions comprise:

$$\ln\left(\frac{\eta}{T}\right) = -a\ln(T_{2GM-intrinsic}) + b,$$

where $\ln(T_{2GM-intrinsic})$=HI*$\ln(T_{2GM})$+(1−HI)*ln(f (0≤t≤$T_E$), where f(0≤t≤$T_E$) is a function that relates a $T_2$ distribution at time t that is less than the echo spacing time during NMR acquisition, $T_{2GM}$ is the NMR relaxation time geometric mean for the oil sample, $T_E$ is the echo spacing time, and a, b are the fit parameters.

In Example 8, the subject matter of Examples 1-7 can further include wherein the NMR relaxation time distribution data comprises NMR $T_1$ relaxation time and/or NMR $T_2$.

In Example 9, the subject matter of Examples 1-8 can further include obtaining the NMR $T_2$ by measuring $T_2$ relaxation as a function of temperature and echo spacing time.

In Example 10, the subject matter of Examples 1-9 can further include wherein the NMR relaxation time geometric mean comprises NMR relaxation time geometric mean $T_{2GM}$.

In Example 11, the subject matter of Examples 1-10 can further include wherein the set of viscosity data is obtained from heavy oil samples having a viscosity in a range greater than 100 cP.

Example 12 is a nuclear magnetic resonance (NMR) device, comprising: an NMR unit to transmit electromagnetic energy and receive NMR secondary electromagnetic field responses associated with the electromagnetic energy; and control circuitry coupled to the NMR unit, the control circuitry to measure NMR relaxation time distributions for oil in a formation based on the received secondary electromagnetic field responses and determine a viscosity of the oil in the formation based on a relationship between a set of viscosity data and an NMR relaxation time geometric mean intrinsic value that is determined based on a relationship between a set of viscosity data for a plurality of oil samples and an NMR relaxation time geometric mean for the plurality of oil samples.

In Example 13, the subject matter of Example 12 can further include wherein the controller is further to determine the set of viscosity data and NMR T2 data for the plurality of oil samples as a function of echo spacing time and temperature.

In Example 14, the subject matter of Examples 12-13 can further include wherein the controller is further to determine the set of viscosity data, NMR T2 data and a hydrogen index for the plurality of oil samples.

In Example 15, the subject matter of Examples 12-14 can further include wherein the controller is further to execute a non-linear regression analysis to model a correlation between the set of viscosity data and a geometric mean for the NMR T2.

In Example 16, the subject matter of Examples 12-15 can further include wherein the viscosity data comprises a temperature range of the plurality of oil samples, a heating or cooling rate of the plurality of oil samples, and/or a rotation frequency of parallel plates of the plurality of oil samples.

In Example 17, the subject matter of Examples 12-16 can further include wherein the NMR relaxation time geometric mean is a NMR T2 geometric mean (T2GM) and the controller is further to determine the NMR T2GM from a T2 distribution.

Example 18 is a system, comprising: a downhole tool housing including a nuclear magnetic resonance (NMR) tool, the NMR tool comprising: an NMR unit comprising a transmitter to transmit NMR signals and a receiver to receive secondary electromagnetic field responses from oil in a formation in response to the transmitted NMR signals; and control circuitry coupled to the NMR unit, the control circuitry to measure NMR relaxation time distributions for oil in a formation based on the received secondary electromagnetic field responses and determine a viscosity of the oil in the formation based on a relationship between a set of viscosity data and an NMR relaxation time geometric mean intrinsic value that is determined based on a relationship between a set of viscosity data for a plurality of oil samples and an NMR relaxation time geometric mean for the plurality of oil samples.

In Example 19, the subject matter of Example 18 can further include wherein the NMR tool is disposed in a wireline tool or a drill string tool.

In Example 20, the subject matter of Examples 18-19 can further include wherein the control circuitry is to perform a non-linear regression analysis to model a correlation between the set of viscosity data and the NMR relaxation time geometric mean by using a power law function.

The detailed description refers to the accompanying drawings that show, by way of illustration and not limitation, various embodiments in which the invention may be practiced. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The detailed description is, therefore, not to be taken in a limiting sense.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description. Combinations of the above embodiments and other embodiments will be apparent to those of ordinary skill in the art upon studying the above description.

What is claimed is:

1. A method, comprising:
    transmitting electromagnetic energy into a formation;
    measuring NMR relaxation time distribution data for oil in the formation based on secondary electromagnetic field responses associated with the electromagnetic energy; and
    determining a viscosity of the oil in the formation based on a correlation between a set of viscosity data and an NMR relaxation time geometric mean intrinsic value of distribution data; wherein the NMR relaxation time geometric mean intrinsic value of distribution data is derived from an echo spacing time ($T_E$) and/or a hydrogen index (HI).

2. The method of claim 1, further comprising:
    obtaining the set of viscosity data and nuclear magnetic resonance (NMR) relaxation time distribution data for a plurality of oil samples;
    determining the NMR relaxation time geometric mean intrinsic value for the distribution data; and
    determining the correlation between the set of viscosity and the NMR relaxation time geometric mean for the NMR relaxation time distribution data.

3. The method of claim 2, further comprising:
    obtaining hydrogen indexes for the plurality of oil samples;
    performing a non-linear regression analysis to model the correlation between the set of viscosity data and the NMR relaxation time geometric mean intrinsic value; and
    obtaining fit parameters based on the non-linear regression analysis.

4. The method of claim 1, further comprising:
    obtaining the viscosity data and the NMR relaxation time distribution as a function of echo spacing time and temperature of the oil sample; and
    performing a non-linear regression analysis and obtaining fit parameters to model the correlation between the set of viscosity data and the NMR relaxation time geometric mean as a function of the echo spacing time.

5. The method of claim 4, further comprising using one or more correlation functions to model the correlation between the set of viscosity data and the NMR relaxation time geometric mean intrinsic value.

6. The method of claim 5, wherein the one or more correlation functions comprise:

$$\frac{\eta}{T} \sim \left(\frac{1}{T_{2GM} + cT_E + d}\right)^{1/(-aT_E+b)} \text{ and/or}$$

$$\frac{\eta}{T} \sim \left(\frac{1}{T_{2GM}}\right)^{1/(-eT_E+f)},$$

where $\eta$ is viscosity of an oil sample, T is a temperature of the oil sample, $T_{2GM}$ is the NMR relaxation time geometric mean for the oil sample, $T_E$ is the echo spacing time, and a, b, c, d, e and f are the fit parameters.

7. The method of claim 5, wherein the one or more correlation functions comprise:

$$\ln\left(\frac{\eta}{T}\right) = -a\ln(T_{2GM-intrinsic}) + b,$$

where $\ln(T_{2GM-intrinsic}) = HI*\ln(T_{2GM}) + (1-HI)*\ln(f(0 \le t \le T_E))$, where $f(0 \le t \le T_E)$ is a function that relates a $T_2$ distribution at time t that is less than the echo spacing time during NMR acquisition, $T_{2GM}$ is the NMR relaxation time geometric mean for the oil sample, $T_E$ is the echo spacing time, and a, b are the fit parameters.

8. The method of claim 1, wherein the NMR relaxation time distribution data comprises NMR $T_1$ relaxation time and/or NMR $T_2$.

9. The method of claim 8, further comprising obtaining the NMR $T_2$ by measuring $T_2$ relaxation as a function of temperature and echo spacing time.

10. The method of claim 1, wherein the NMR relaxation time geometric mean comprises NMR relaxation time geometric mean $T_{2GM}$.

11. The method of claim 1, wherein the set of viscosity data is obtained from heavy oil samples having a viscosity in a range greater than 100 cP.

12. A nuclear magnetic resonance (NMR) device, comprising:
an NMR unit to transmit electromagnetic energy and receive NMR secondary electromagnetic field responses associated with the electromagnetic energy; and
control circuitry coupled to the NMR unit, the control circuitry to measure NMR relaxation tune distributions for oil in a formation based on the received secondary electromagnetic field responses and determine a viscosity of the oil in the formation based on a relationship between a set of viscosity data and an NMR relaxation time geometric mean intrinsic value that is determined based on a relationship between a set of viscosity data for a plurality of oil samples and an NMR relaxation time geometric mean for the plurality of oil samples.

13. The NMR device of claim 12, wherein the controller is further to determine the set of viscosity data and NMR $T_2$ data for the plurality of oil samples as a function of echo spacing time and temperature.

14. The NMR device of claim 12, wherein the controller is further to determine the set of viscosity data, NMR $T_2$ data and a hydrogen index for the plurality of oil samples.

15. The NMR device of claim 12, wherein the controller is further to execute a non-linear regression analysis to model a correlation between the set of viscosity data and a geometric mean for the NMR $T_2$.

16. The NMR device of claim 12, wherein the viscosity data comprises a temperature range of the plurality of oil samples, a heating or cooling rate of the plurality of oil samples, and/or a rotation frequency of parallel plates of the plurality of oil samples.

17. The NMR device of claim 12, wherein the NMR relaxation time geometric mean is a NMR $T_2$ geometric mean ($T_{2GM}$) and the controller is further to determine the NMR $T_{2GM}$ from a $T_2$ distribution.

18. A system, comprising:
a downhole tool housing including a nuclear magnetic resonance (NMR) tool, the NMR tool comprising:
an NMR unit comprising a transmitter to transmit NMR signals and a receiver to receive secondary electromagnetic field responses from oil in a formation in response to the transmitted NMR signals; and
control circuitry coupled to the NMR unit, the control circuitry to measure NMR relaxation time distributions for oil in a formation based on the received secondary electromagnetic field responses and determine a viscosity of the oil in the formation based on a relationship between a set of viscosity data and an NMR relaxation time geometric mean intrinsic value that is determined based on a relationship between a set of viscosity data for a plurality of oil samples and an NMR relaxation time geometric mean for the plurality of oil samples.

19. The system of claim 18, wherein the NMR tool is disposed in a wireline tool or a drill string tool.

20. The system of claim 18, wherein the control circuitry is to perform a non-linear regression analysis to model a correlation between the set of viscosity data and the NMR relaxation time geometric me by using a power law function.

* * * * *